United States Patent
Hossain et al.

(10) Patent No.: US 12,251,101 B1
(45) Date of Patent: Mar. 18, 2025

(54) SURGICAL NANO-BIOTHREAD MADE FROM CELLULOSE FIBER

(71) Applicant: IMAM MOHAMMAD IBN SAUD ISLAMIC UNIVERSITY, Riyadh (SA)

(72) Inventors: Abm Sharif Hossain, Riyadh (SA); Hassan Ahmed Alrudayni, Riyadh (SA); Mohammed Saad Aleissa, Riyadh (SA); Fazliny Abdul Rahman, Kota Damansara (MY)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 18/735,698

(22) Filed: Jun. 6, 2024

(51) Int. Cl.
| | |
|---|---|
| *D01F 2/02* | (2006.01) |
| *A61B 17/06* | (2006.01) |
| *A61L 17/10* | (2006.01) |
| *C08B 15/00* | (2006.01) |
| *C08K 5/00* | (2006.01) |
| *C08L 1/02* | (2006.01) |
| *D01D 1/02* | (2006.01) |
| *D01F 1/06* | (2006.01) |
| *D01F 1/10* | (2006.01) |
| *A61B 17/00* | (2006.01) |

(52) U.S. Cl.
CPC ........ *A61B 17/06166* (2013.01); *A61L 17/10* (2013.01); *C08B 15/00* (2013.01); *C08K 5/0041* (2013.01); *C08L 1/02* (2013.01); *D01D 1/02* (2013.01); *D01F 1/06* (2013.01); *D01F 1/10* (2013.01); *D01F 2/02* (2013.01); *A61B 2017/00004* (2013.01); *C08L 2201/06* (2013.01); *C08L 2203/02* (2013.01); *C08L 2203/12* (2013.01); *C08L 2205/025* (2013.01); *C08L 2205/035* (2013.01); *D10B 2201/22* (2013.01); *D10B 2509/04* (2013.01)

(58) Field of Classification Search
CPC .... A61B 17/06166; A61B 2017/00004; A61L 17/10; C08B 15/00; C08K 5/0041; C08L 1/02; C08L 2201/06; C08L 2203/02; C08L 2203/12; C08L 2205/025; C08L 2205/035; D01D 1/02; D01F 1/10; D01F 2/02; D10B 2201/22; D10B 2509/04
See application file for complete search history.

(56) References Cited

U.S. PATENT DOCUMENTS 5,958,182 A    9/1999   Hondroulis et al.

FOREIGN PATENT DOCUMENTS

| GB | 253971 A | 12/2016 | | |
|---|---|---|---|---|
| IN | 244800 B | 12/2010 | | |
| JP | 2002146219 A | 5/2002 | | |
| KR | 100863218 B1 | 10/2008 | | |
| WO | WO2012/068402 | * | 5/2012 | ........... D01D 5/0069 |
| WO | WO-2012068402 A2 | * | 5/2012 | ....... A61B 17/00234 |

OTHER PUBLICATIONS

Sharif Hossain AB, Ibrahim NA, ALEissa MS. "Nano-cellulose derived bioplastic biomaterial data for vehicle bio-bumper from banana peel waste biomass". Data Brief. May 25, 2016;8:286-94.
Tavares, T.D.; Antunes, J.C.; Ferreira, F.; Felgueiras, H.P., "Biofunctionalization of Natural Fiber-Reinforced Biocomposites for Biomedical Applications", Biomolecules 2020, 10, 148.
Kalita H, Hazarika A, Kandimalla R, Kalita S, Devi R. "Development of banana (*Musa balbisiana*) pseudo stem fiber as a surgical bio-tool to avert post-operative wound infections", RSC Adv. Oct. 31, 2018;8(64):36791-36801.
Acquavia, M.A.; Pascale, R.; Martelli, G.; Bondoni, M.; Bianco, G. "Natural Polymeric Materials: A Solution to Plastic Pollution from the Agro-Food Sector", Polymers 2021, 13, 158.
Zamora-Mendoza L, Gushque F, Yanez S, Jara N, Álvarez-Barreto JF, Zamora-Ledezma C, Dahoumane SA, Alexis F. "Plant Fibers as Composite Reinforcements for Biomedical Applications", Bioengineering (Basel). Jul. 5, 2023;10(7):804.
Bacakova L, Pajorova J, Bacakova M, Skogberg A, Kallio P, Kolarova K, Svorcik V. "Versatile Application of Nanocellulose: From Industry to Skin Tissue Engineering and Wound Healing. Nanomaterials (Basel)". Jan. 29, 2019;9(2):164.

* cited by examiner

Primary Examiner — Monica A Huson
(74) Attorney, Agent, or Firm — Nath, Goldberg & Meyer; Joshua B. Goldberg

(57) ABSTRACT

A method of making a surgical biothread from natural cellulose fiber is provided. The method includes making nanoscale cellulose using acid hydrolysis and pyrolysis of a mixture of palm tree stems and banana flower bracts; mixing the nanoscale cellulose with a plasticizer to obtain a nanoscale polymer; and casting the nanoscale polymer using a syringe and needle to obtain the biothread.

10 Claims, No Drawings

SURGICAL NANO-BIOTHREAD MADE FROM CELLULOSE FIBER

BACKGROUND

Field

The disclosure of the present patent application relates to surgical nano-biothread made from cellulose fiber and particularly to a method of making a surgical nano-biothread from a mixture of palm tree and banana flower waste bract derived cellulose.

Description of Related Art

With the increasing environmental awareness and growing importance of fabrics, palm trees fibers have been innovatively recognized for all their good qualities. The application of such palm tree fibers is increasing in various fields, such as the apparel garments industries.

Traditionally, surgeons have used a synthetic suture thread produced from oil and petroleum-based materials. These traditional methods of producing surgical thread are expensive and the resulting thread is not biodegradable. Accordingly, a second surgery is typically required to remove these currently available surgical threads from a patient.

Thus, a surgical nano-biothread made from a natural material solving the aforementioned problems is desired.

SUMMARY

The present subject matter relates to a surgical nanobiothread made from cellulose fiber. In an embodiment, the surgical nanobiothread can be made by a process including making nanoscale cellulose using acid hydrolysis and pyrolysis; mixing the nanoscale cellulose with a plasticizer to obtain a nanoscale polymer; and casting the nanoscale polymer using a syringe and needle to obtain the surgical nanobiothread.

These and other features of the present subject matter will become readily apparent upon further review of the following specification.

DETAILED DESCRIPTION

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a surgical nanobiothread made from a cellulose blend. In an embodiment, the surgical nanobiothread can be made by a process including making a nanocomposite cellulose blend derived from plant lignocellulose using acid hydrolysis and pyrolysis; mixing the nanocomposite cellulose blend with a plasticizer to obtain a nanoscale polymer; and casting the nanoscale polymer using a syringe and needle to obtain the surgical nanobiothread. The obtained surgical nanobiothread can be used as a suture material in medical and dental surgeries.

In one embodiment, the nanoscale cellulose blend can include a lignocellulose such as, by way of non-limiting example, a nano-cellulose obtained from palm tree stem fiber. In another embodiment, the nanoscale cellulose blend can include a nanocomposite cellulose biopolymer. This nanocomposite cellulose biopolymer can be obtained, by way of non-limiting example, from banana flower waste bract fiber. The resultant nanoscale cellulose blend can be used to obtain a bio-thread useful for medical and dental surgery.

In an embodiment, the nanoscale cellulose may be made by gathering waste palm tree stems and waste banana flower bracts, cutting the waste palm tree stem and waste banana flower bracts, washing the cut waste palm tree stem and cut waste banana flower bracts with water, followed by bleaching with sodium hypochlorite, and using acid hydrolysis to obtain nanoscale particles from the waste palm tree stem and waste banana flower bracts.

In certain embodiments, the washing step may be conducted by soaking the cut plant material, i.e., the cut waste palm tree stem and cut waste banana flower bracts, in water for a suitable amount of time. One non-limiting example of a suitable amount of time in this regard is about 4 hours. In another embodiment, the water can be distilled water.

In another embodiment, the bleaching with sodium hypochlorite can be conducted by washing the cut plant material, after the washing with water, with sodium hypochlorite for a suitable amount of time. One non-limiting example of a suitable amount of time in this regard is about 4 hours.

In other embodiments, the acid hydrolysis may be conducted using about 75% to about 80% sulphuric acid. This acid hydrolysis can effectively convert any microparticles of the cellulose blend to nanoparticles. After acid hydrolysis, the plant material may further be pyrolyzed in an oven, by way of non-limiting example, at about 135° C. for about 3 hours, to obtain the nanoscale cellulose. In certain embodiments, the pyrolysis can be conducted in a 30 psi environment.

In an embodiment, the nanoscale cellulose can be mixed with various suitable components to obtain a mixture which can be used to form the surgical nano-biothread. In this regard, forming the mixture may include mixing about 48% v/v of the nanoscale cellulose (derived from palm tree stem and banana flower waste bract) with one or more plasticizers, for example, one or more organic plasticizers, such as, by way of non-limiting example, polyvinyl chloride (about 5% v/v) with pure cellulose 8% v/v (i.e., cellulose that is not nanoscale); or starch (about 8% v/v) as plasticizes. This step may optionally include the addition of one or more dyes. By way of non-limiting example, this step may include the addition of an orange and/or mango peel dye (cumulatively up to about 5% v/v) and/or a turmeric organic dye (up to about 5% v/v). This step may optionally include the addition of other organic substances (as natural or organic plasticizers), including but not limited to one or more of aloe vera gel (up to about 4% v/v), flaxseed gel (up to about 4% v/v), fresh arabica gel (up to about 4% v/v), and waste cooking oil-based glycerin (up to about 5% v/v). Finally, this step may also include the addition of one or more natural glues (up to about 4% v/v), such fresh gum from a *Lannea* sp. (*Lannea coromandelica*, otherwise known as Kafila), or the like.

Once formed, the mixture can then be cast using, e.g., a syringe and a needle, and allowed to dry to form the resultant surgical nano-biothread. In an embodiment, the drying step can be conducted at about 80° C., for example, in an oven.

In an embodiment, the nanobiothread made according to these methods may be useful as an alternative to traditional surgical suturing materials. In another embodiment, the present nanobiothread is biodegradable in situ, meaning it does not need to be removed following surgical stitching, but instead will dissolve in situ as a biodegradable biomaterial. Accordingly, this represents a significant advantage over other currently available surgical threads or stiches, which may require a second surgery to be removed from a patient to which the thread was initially applied.

The present disclosure may be better understood in view of the following examples.

Example 1

Waste palm tree (*Trachycarpus* sp.) stems and waste banana flower bracts were cut up into small pieces of plant material. The plant material was soaked in distilled water for about 4 hours, washed with sodium hypochlorite for about 4 hours, and acid hydrolyzed using 75% sulphuric acid and pyrolyzed in an oven at about 135° C. for about 3 hours to obtain nanoscale cellulose. The nanoscale cellulose (about 48% v/v from an organic sample [palm tree stem and banana flower waste bract derived cellulose]) was then mixed with polyvinyl chloride (about 5% v/v), pure cellulose (about 8% v/v), starch (about 8% v/v), aloe vera gel (about 4% v/v), flaxseed gel (about 4% v/v), fresh arabica gel (about 4% v/v), natural or organic glue or adhesive (about 4% v/v kafila, *Lannea* sp. Fresh gum sap), waste cooking oil-based glycerin (about 5% v/v), orange and mango peel dyes (about 5% v/v) and turmeric organic dye (about 5% v/v), with the balance of the volume being water. This mixture was then cast using a syringe and a needle and allowed to dry to form the surgical nano-biothread.

The resulting surgical nanobiothread was then tested by various methods, including confirmation of nanocellulose formation by transmission electron microscopy, determination of water absorption according to ASTM (American Standard for Testing and Materials) D570, odor testing according to ASTM D3801, and determination of tensile strength by ASTM D2256.

The results showed that the nanobiothread material had a 30 cm length and a diameter of about 30 nm and that negligible water (15%) was absorbed by the nanobiothread material. It was also determined that there was no thread odor detected when using the standard ASTM burning test as compared to a commercially available synthetic surgical thread (suture). The shrinkage and fracture (no increase or decrease in shape or size), tensile strength (80 Mpa), tensile modulus (0.5 GPa), breaking weight (2 kg), pH, nanoparticle measurement and cellulose content of the present nanocomposite thread were all determined to fall within the ASTM standard value range for surgical suture.

An organic color test was also conducted. Chemical elements of the nanobiothread were analyzed and positive results were found for K, Ca, $CO_3^-$, Cl, Na, Si, Fe, Pb, Cu & Al.

Based on these results it was determined that the nanobiothread constitutes an innovative organic nanocomposite thread polymer biomaterial using palm tree fiber in combination with banana flower waste bract fiber as cellulose and the nanobiothread may be useful for medical and dental surgical (Suture) purposes. Moreover, this organic surgical biothread biomateral appears to be well-suited for industrial scale production.

It is to be understood that the surgical biothread made from cellulose fiber is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of making a nanobiothread, comprising:
   a. providing a mixture of waste palm tree stems and waste banana flower bracts;
   b. acid hydrolyzing the mixture;
   c. pyrolyzing the mixture to obtain a nanoscale cellulose blend;
   d. mixing the nanoscale cellulose blend with a plasticizer to obtain a nanoscale polymer; and
   e. casting the nanoscale polymer using a syringe and needle to obtain the nanobiothread.

2. The method of claim 1, further comprising washing the mixture and bleaching the mixture prior to acid hydrolyzing the mixture.

3. The method of claim 2, wherein washing the mixture comprises soaking the mixture in water for about 4 hours.

4. The method of claim 2, wherein bleaching the mixture comprises soaking the mixture in sodium hypochlorite for about 4 hours.

5. The method of claim 1, wherein acid hydrolyzing the mixture comprises adding about 75% to about 80% sulphuric acid to the mixture.

6. The method of claim 1, wherein pyrolyzing the mixture is conducted in an oven at about 135° C. for about 3 hours.

7. The method of claim 1, wherein mixing the nanoscale cellulose blend with a plasticizer comprises mixing about 48% of the nanoscale cellulose blend with about 5% v/v polyvinyl chloride, about 8% v/v pure cellulose and about 8% v/v starch.

8. The method of claim 7, further comprising mixing the nanoscale cellulose blend with one or more dyes selected from the group consisting of 5% v/v orange and mango peel dye, 5% v/v turmeric organic dye, and a combination thereof.

9. The method of claim 7, further comprising mixing the nanoscale cellulose blend with one or more components selected from the group consisting of 4% v/v aloe vera gel, 4% v/v flaxseed gel, 4% v/v arabica gel, 5% v/v waste cooking oil-based glycerin, and a combination thereof.

10. The method of claim 7, further comprising mixing the nanoscale cellulose blend with 4% v/v natural gum (*Lannea* sp.).

* * * * *